(12) United States Patent
Liu et al.

(10) Patent No.: US 8,404,477 B2
(45) Date of Patent: Mar. 26, 2013

(54) BACILLUS LICHENIFORMIS AND METHOD FOR DETOXIFICATION OF ZEARALENONE

(75) Inventors: Je-Ruei Liu, Taipei (TW); Ping-Jung Yi, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/790,322

(22) Filed: May 28, 2010

(65) Prior Publication Data

US 2011/0171722 A1 Jul. 14, 2011

(30) Foreign Application Priority Data

Jan. 11, 2010 (TW) .............................. 99100613 A

(51) Int. Cl.
*C12N 1/20* (2006.01)
(52) U.S. Cl. .................. 435/252.5; 435/262.5
(58) Field of Classification Search ................ 435/252.5
See application file for complete search history.

(56) References Cited

PUBLICATIONS

Zinedine et al., Review on the toxicity, occurrence, metabolism, detoxification, regulations and intake of zearalenone: An oestrogenic mycotoxin, 2007, Food and Chemical Toxicology 45:1-18.*
Yi et al., Isolation and characterization of a *Bacillus licheniformis* strain capable of degrading zearalenone, 2010, World Journal of Microbiology and Biotechnology 27(5): 1035-1043.*
Cho et al., In vitro degradation of zearalenone by *Bacillus subtilis*, 2010, Biotechnol. Lett. 32: 1921-1924.*
P.J. Yi et al, Characterization of a Xylanase-Producing *Bacillus licheniformis* Strain Capable of Detoxifying of Mycotoxins, Journal of the Chinese Society of Animal Science, 2009, 38 (Suppl.).

* cited by examiner

*Primary Examiner* — Jon P Weber
*Assistant Examiner* — Robert Yamasaki
(74) *Attorney, Agent, or Firm* — WPAT, P.C.; Anthony King

(57) ABSTRACT

The present invention discloses an isolated pure culture of a novel strain CK1 of *Bacillus licheniformis*, DSM 025954, capable of detoxification of zearalenone (ZEN). Using physiological, biochemical, morphological identification and 16S rRNA gene sequence analysis methods, the strain CK1 was identified as *Bacillus licheniformis*. Through extracellular xylanase, CMCase protease assays and evaluations for zearalenone detoxification, the strain CK1 strain was identified to possess good ZEN-detoxifying ability, to be non-hemolytic, non-enterotoxin producing, and displayed high levels of extracellular xylanase, cellulase, and protease activities. Accordingly, *Bacillus licheniformis* CK1 can be applied as food and feed supplement for bio-detoxification of ZEN.

7 Claims, 9 Drawing Sheets

BACILLUS LICHENIFORMIS AND METHOD FOR DETOXIFICATION OF ZEARALENONE

BACKGROUND OF THE INVENTION

1. Field of the Invention

The present invention relates to a novel strain of *Bacillus licheniformis*, in particular to a zearalenone (ZEN)-detoxifying *Bacillus licheniformis* CK1 (DSM 025954).

2. The Prior Arts

Fungal toxin is a major problem in cereal grains throughout the world, which causes the health problems for human and livestock, and huge economical losses. These toxins include aflatoxins, fumonisins, ochratoxins, tremorgenic toxins, trichothecenes, and zearalenone. Zearalenone (ZEN) is a potent non-steroid estrogenic metabolite, produced by the *Fusarium graminearum, F. culmorum, F. cerealis, F. equiseti, F. crookwellense* and *F. semitectum* common in soil in warm areas. Zearalenone causes reproductive disorders and has been implicated in hyperoestrogenic syndromes in humans. Though ZEN was not classified by the WHO-International Agency for Research on Cancer (IARC) in group 3, not classifiable as to its carcinogenicity to humans, it was reported to be hepatotoxic, hematotoxic, immunotoxic and genotoxic in studies.

Many studies have focused on the tests for the above mentioned mycotoxins to prevent the contamination on products. However, the best solution is to remove the toxins through biochemical degradation, which may retain the nutrition and flavor in a mild detoxifying way without using harmful chemicals.

Application of microorganisms in degradation of the toxin in foods or feeds is a well known technology. Biological detoxification can be used to decrease or remove contamination of mycotoxins in a highly efficient, specific and non-environmental affecting way. There are two applications in treating fungi contaminated foods or feeds: mycotoxins biodegradation and inhibition of absorption of mycotoxins. *Butyrivibrio fibrisolvens, Gliocladium roseum, Trichosporon mycotoxinivorans* and some rumen protozoa can degrade the mycotoxins into non-toxic or slightly toxic products. *Lactobacillus rhamnosus* and *Saccharomyces cerevisiae* can inhibit absorption of mycotoxins through binding to the cell walls of microorganisms in the gastrointestinal tract.

*Bacillus licheniformis* is a saprophytic bacterium that is widespread in nature. The enzymes of *Bacillus licheniformis* for industrial production include amylase and protease. According to previous studies, they have great potential to be used as beneficial microorganisms for human or feed supplements. Researchers have reported that *Bacillus licheniformis* increased the function of immune systems, increased weights, decreased the chance of diarrhea in mice and improved the feed-conversion efficiency in pigs when used as beneficial microorganisms. In addition, *Bacillus licheniformis* was found to inhibit the growth of *Aspergillus* and degrade aflatoxins B1 (AFB1) and ochratoxins A (OTA). However, there is no report regarding the application of *Bacillus licheniformis* in detoxifying zearalenone.

SUMMARY OF THE INVENTION

No *Bacillus licheniformis* strain was applied in detoxification of zearalenone (ZEN) though microorganisms are applied in degradation of the toxin in foods or feeds as a well known technology and *Bacillus licheniformis* contains many enzymes such as proteases and amylases. In addition, the concerns on enterotoxin-producing and hemolytic problems are existed in microorganisms for biodegradation.

Therefore, the objective of the present invention is to provide a zearalenone (ZEN)-detoxifying *Bacillus licheniformis*, wherein a sample of the *Bacillus licheniformis* has been deposited in the Deutsche Sammlung von Mikroorganismen and Zellkulturen GmbH (DSMZ) located at Inhoffenstr. 7B D-38124 Braunschweig with an accession number DSM 025954 deposited on Apr. 26, 2012.

Another objective of the present invention is to provide for detoxifying zearalenone (ZEN) comprising using the *Bacillus licheniformis*.

To solve the problems in prior art, the present invention provides a novel CK1 strain was isolated from soils and identified to be *Bacillus licheniformis* using morphological and genetic analysis methods. Through extracellular xylanase, CMCase, protease assays and evaluations for ZEN detoxification, CK1 strain was shown to have good detoxification effects on ZEN, and displayed high levels of extracellular xylanase, cellulase, and protease activities.

Using physiological, biochemical, morphological and 16S rRNA gene sequence analysis methods, the strain CK1 in the present invention was identified to be *Bacillus licheniformis*. In addition, the strain CK1 was shown to have good detoxifying ability toward zearalenone (ZEN). The strain CK1 in the present invention is the first *Bacillus licheniformis* being disclosed to have such detoxifying ZEN effects in the present research field. After biochemical and genetic analysis methods, the strain CK1 was shown to be non-hemolytic, non-enterotoxin producing, and have good ZEN detoxification effects on cereals, which is good supplement for food and feed to promote the lysis of cellulose, semi-cellulose and protein. In addition, this method of biological detoxification can be used to decrease or remove contamination of mycotoxins in a highly efficient, specific and non-environmental affecting way.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention to be made later are described briefly as follows, in which.

DETAILED DESCRIPTION OF THE PREFERRED EMBODIMENT

Example 1

Morphological and Molecular Identification of *Bacillus licheniformis* CK1

(1) Strains

The novel strain CK1 was isolated from soils in Experimental Farm College of Bio-Resources and Agriculture, National Taiwan University according to Petchkongkaew et al. (2008). Single colonies screened from samples were transferred to LB (Luria-Bertani) agar plate (Difco Laboratories) containing 0.5% (w/v) oat spelt xylan (Sigma-Aldrich Co.) at 37° C. cultivated for 24 h, followed by xylanase assay with Congo Red plate staining A yellow ring resulting from xylan hydrolysis appeared around positive colonies. *Bacillus licheniformis* CK1 in the present invention showed the highest level of xylanase activity was selected for further analysis.

*Bacillus licheniformis* ATCC 14580 was purchased from American Type Culture Collection (ATCC, Manassas, Va.) as a control. All the strains were cultivated in LB at 37° C. Agar plates were prepared by adding agar in the ratio of 1.5% W/V.

(2) Morphological Traits

The strain CK1 was cultivated and observed in blood agar plates (Merck, Darmstadt, Germany) at 37° C. for 24 h. CK1 was observed under a microscope for morphological analysis after the cells were cultivated in LB at 37° C., fixed with ethanol during mid-log phase, and stained with DAPI staining (Waldech et al., 2006). The cells were also observed after staining with the Gram stain (Sigma-Aldrich Co.). Biochemical analysis on different carbon sources for the strain CK1 was performed with an API 50 CHB system (bioMerieux, Inc.).

(3) Molecular Identification

The genomic DNA of the strain CK1 was extracted using DNeasy Blood & Tissue kit (Qiagen Inc.). 16S rRNA was amplified using primer pair 16S-27f (SEQ ID NO: 1) and 16S-1492r (SEQ ID NO: 2) through PCR amplification, followed by sequence analysis. Sequence alignment of 16S rRNA gene from nucleotide 54 to 510 (including the V1 and V3 variable regions) was carried out using BioEdit Sequence Alignment Editor program (Hall, 1999). The neighbor-joining method was used to construct the phylogenetic tree with the Clustal W program (Thompson et al., 1994). Tree figures were generated using the TreeView program (Page, 1996).

(4) Identification of *Bacillus licheniformis* CK1

Figure 1:
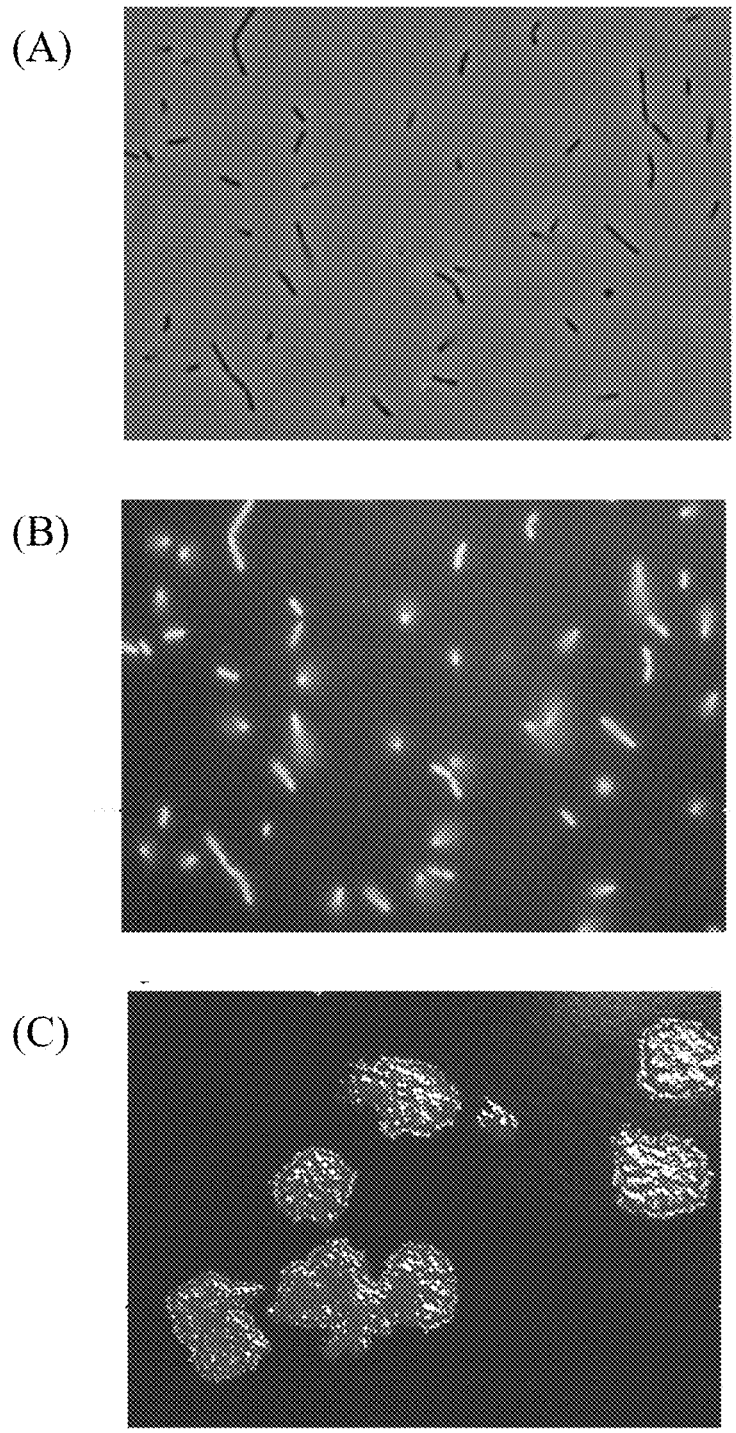
FIG. 1A and FIG. 1B display bacterial morphology of the strain CK1 under phase contrast microscope and fluorescent microscope respectively.
FIG. 1C shows the colonies in blood agar plate.

The novel strain CK1 containing the highest xylanase activity was deposited in the Deutsche Sammlung von Mikroorganismen and Zellkulturen GmbH (DSMZ) with an accession number DSM 025954. Referring to FIGS. 1A to 1C, FIG. 1A and FIG. 1B showed the bacterial morphology of the strain CK1 under phase contrast microscope and fluorescent microscope respectively; and FIG. 1C shows the colonies in blood agar plate. Colonies were rough with irregular margins, and non-hemolytic. The strain CK1 was found to be rod-shaped, single or chained distributed, motile and endospore-forming in FIG. 1A and FIG. 1B, which matched the description of *Bacillus licheniformis* according to Bergey's Manual of Systematic Bacteriology (Claus and Berkeley, 1986). Both strains of CK1 and ATCC 14580 were tested using the API system-API 50 CHB kit. The difference between them was very small. As listed in Table 1, both strains could grow in 26 out of 49 different carbohydrates. However, difference in sugar utilization (ribose, galactose, acetylglucosamine, lactose, melibiose) was found. The strain CK1 results of the API 50 CHB databank revealed 99.9% homology to *Bacillus licheniformis*.

TABLE 1

| substrate | strain CK1 | strain ATCC14580 | substrate | strain CK1 | strain ATCC14580 |
|---|---|---|---|---|---|
| Glycerol | + | + | Esculin ferric citrate | + | + |
| Erythritol | − | − | Salicin | + | + |
| D-Arabinose | − | − | D-Cellobiose | + | + |
| L-Arabinose | + | − | D-Maltose | + | + |
| D-Ribose | + | + | D-Lactose | + | − |
| D-Xylose | + | + | Melibiose | − | + |
| L-Xylose | − | − | D-Sucrose | + | + |
| D-Adonitol | − | − | D-Trehalose | + | + |
| Methyl-xylopyranoside | − | − | Inulin | + | + |
| D-Galactose | − | + | D-Melezitose | − | − |
| D-Glucose | + | + | D-Raffinose | + | + |
| D-Fructose | + | + | Amidon/Starch | + | + |
| D-Mannose | + | + | Glycogen | + | + |
| D-Sorbose | + | + | Xylitol | − | − |
| Rhamnose | − | − | Gentiobiose | − | − |
| Dulcitol | − | + | D-Turanose | − | − |
| Inositol | − | − | D-Lyxose | − | − |
| D-Mannitol | + | + | D-Tagatose | + | + |
| D-Sorbitol | + | + | D-Frucose | − | − |
| α-Methyl-D-mannoside | − | − | L-Frucose | − | − |
|  |  |  | D-Arabitol | − | − |
| α-Methyl-D-glucoside | + | + | L-Arabitol | − | − |
|  |  |  | Gluconate | − | − |
| N-Acetylglucosamine | + | − | 2-Ketogluconate | − | − |
|  |  |  | 5-Ketogluconate | − | − |
| Amygdalin | + | + |  |  |  |
| Arbutin | + | + |  |  |  |

Figure 2:
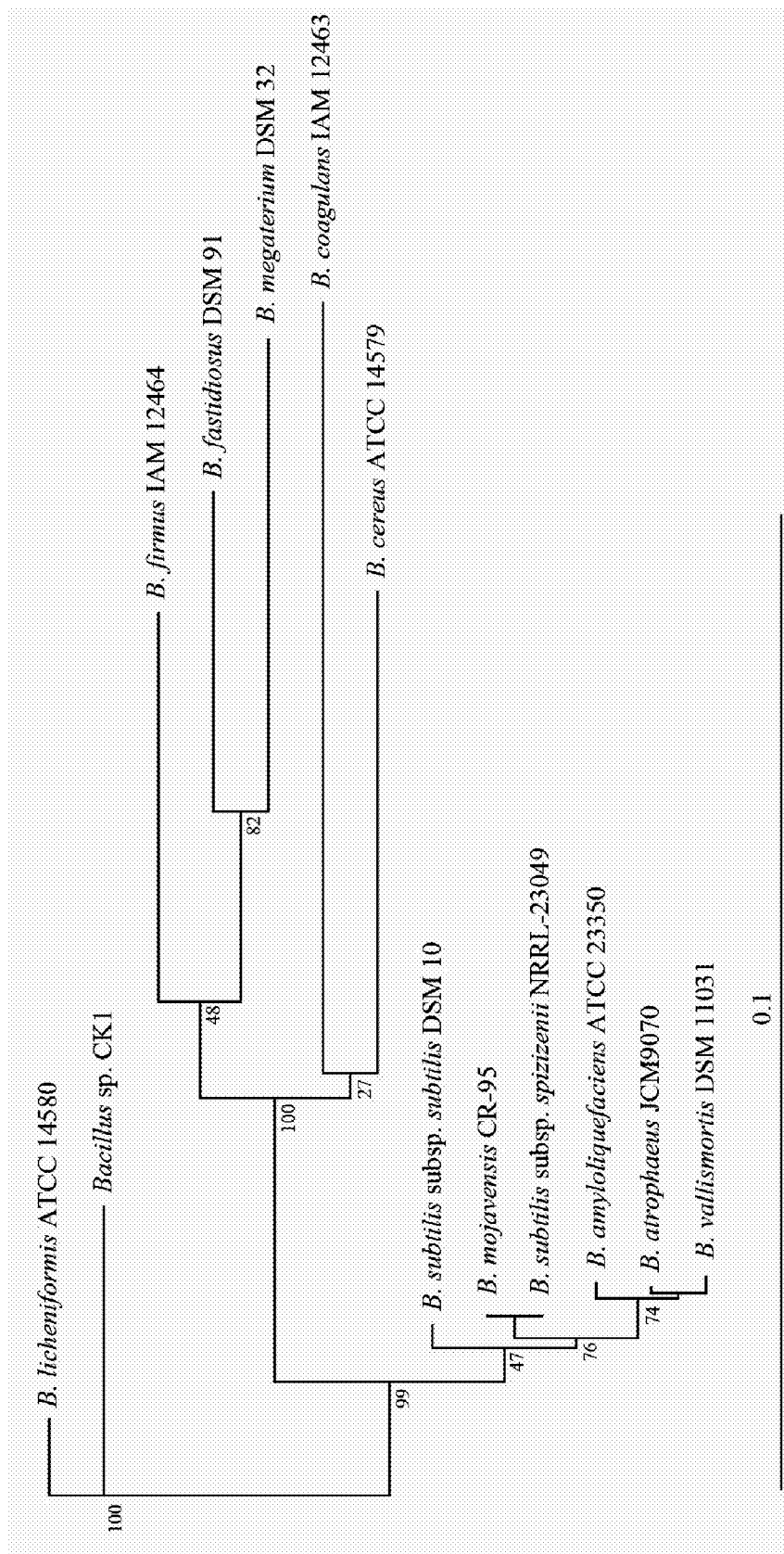
FIG. 2 shows the phylogenetic tree constructed using neighbor-joining method.

Referring to FIG. 2, the phylogenetic tree of 16S rRNA was constructed using neighbor-joining method after the gene sequences (including the V1 and V3 variable regions) from strains CK1 and ATCC 14580 were determined. It showed 96.3% similarity between CK1 and ATCC 14580. Therefore, the strain CK1CK1 was identified to belong to *Bacillus licheniformis* after the observation under microscopes, morphological traits and biochemical tests as well as the 16S rRNA gene sequence analysis methods including the V1 and V3 variable regions.

Example 2

Extracellular Xylanase, CMCase, and Protease Activity of *Bacillus licheniformis*

Overnight culture of strains CK1 and ATCC 14580 were transferred into 10 ml of LB broth in a ratio of 1% and cultivated at 37° C., 250 rpm for 16 h. The cell supernatents were collected after the centrifugation of 5,000×g for 20 min at 4° C., followed by radial diffusion method and enzyme assay.

Radial Diffusion Methods

The extracellular xylanase, CMCase, and protease activities of strains CK1 and ATCC 14580 were assayed using the radial diffusion methods (Teather and Wood, 1982; and Waldeck et al. 2006).

Figure 3:
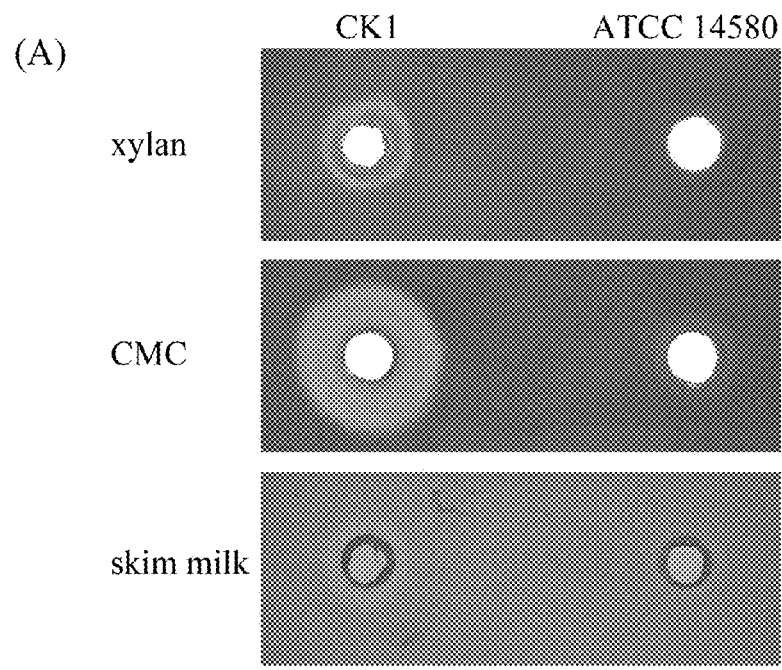
FIG. 3A shows the enzyme activities of the strain CK1 and ATCC 14580 toward various substrates.
FIG. 3B shows the enzyme activities of the strain CK1 and ATCC 14580 after 24 h of fermentation.
Figure 3:
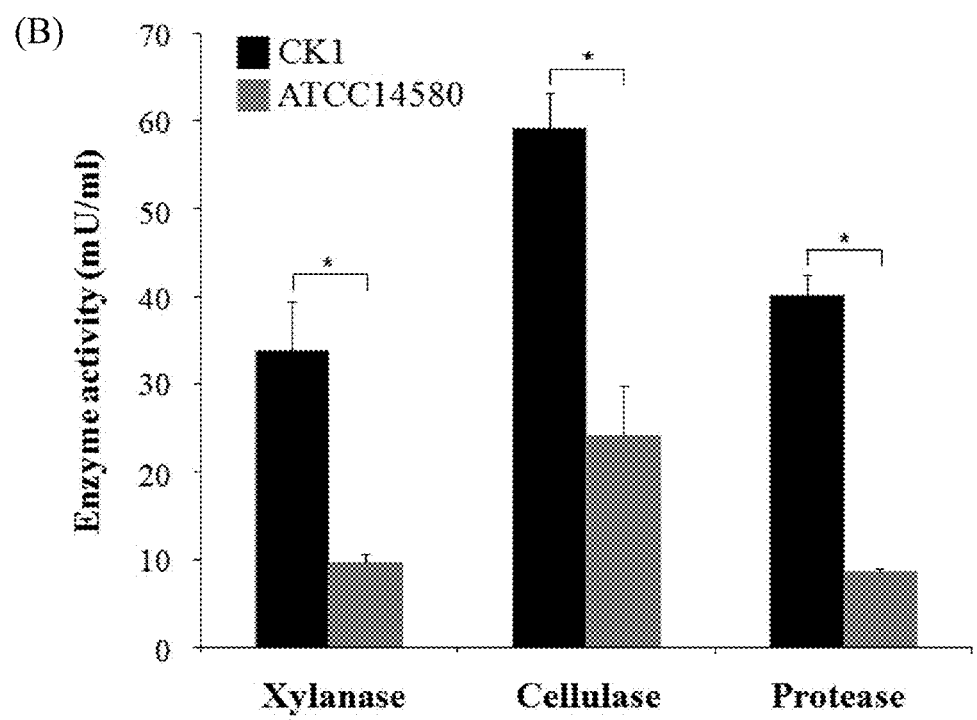

FIG. 3A showed the enzyme activities toward various substrates (xylan, carboxymethyl cellulose (CMC) and skim milk) of strains CK1 and ATCC 14580. The substrate in the medium would be degraded and displayed a clear zone when the bacteria had the enzyme activity. The strain CK1 showed higher activity toward xylan, carboxymethyl cellulose (CMC) and skim milk by showing a larger clear zone when compared to ATCC 14580.

Xylanase, CMCase, and Protease Activity of *Bacillus licheniformis* CK1

Xylanase and CMCase activities were determined using azo-xylan and azo-CMC (Megazyme, Wicklow, Ireland) as substrates according to the instruction. 0.5 ml of sodium acetate (pH 5.0) containing 2% of the staining substrate was added into 0.5 ml of cell supernatent and incubated at 40° C. for 60 min, followed by addition of 2.5 volumes of precipitating buffer (4% sodium acetate trihydrate and 0.4% zinc acetate in 95% ethanol). The solution was centrifuged at 1,000×g for 10 min and the absorbance at 590 nm was read with a spectrophotometer. Enzyme unit was determined with the standard curve provided by the manufacturer. One unit of cellulase activity was defined as the amount of enzyme required to liberate 1 mmol staining dye in one minute from the substrate under the defined condition.

Proteinase activity was determined with the staining dye released from the strain CK1 culture supernatant (Waldeck et al., 2006). 0.5 ml of 100 mM sodium phosphate (pH 7.0) containing 2% (w/v) of the azo-casein was added into 0.5 ml of CK1 cell supernatent and incubated at 40° C. for 60 min, followed by addition of 3 ml of 5% TCA. The solution was centrifuged at 1,000×g for 10 min and the absorbance at 440 nm was read with a spectrophotometer. Enzyme unit was determined with the standard curve provided by the manufacturer. One unit of proteinase activity was defined as the amount of enzyme required to liberate 1 µmol staining dye in one minute from the azo-casein under the defined condition.

Statistic analysis was performed using Statistical Analysis System software package version 9.1 (Statistical Analysis System Institute, 2002). All the results were given in average±standard deviation. Student's t-test was used for the comparison, and P-value<0.05 is considered significant.

FIG. 3B showed the enzyme activities of the strain CK1 and ATCC 14580 after 24 h of fermentation to compare with the results from the radial diffusion method. The strain CK1 showed higher xylanase, CMCase and proteinase activity when compared to ATCC 14580, which matched the result from the radial diffusion method.

Example 3

Growth of *Bacillus licheniformis* Under the Influence of Zearalenone (ZEN)

Zearalenone (Sigma-Aldrich) was dissolved in DMSO as the stock solution. Growth of *Bacillus licheniformis* under the influence of ZEN was studied after 1% of CK1 or ATCC 14580 overnight culture was inoculated into 10 ml of LB broth either containing 2 ppm ZEN or not and incubated at 37° C. with shaking at 250 rpm for 48 h respectively. Samples were taken every 4 h to determine the cell number using standard agar plate count and OD600 measurement.

The strain CK1 reached stationary phase with the cell number of $9.17\pm0.14$ log CFU ml$^{-1}$ (OD600: $2.09\pm0.02$) after incubated in LB at 37° C. for 24 h. ATCC 14580 strain showed similar result as the CK1 strain. No significant difference between the cell counts of CK1 and ATCC 14580 during fermentation.

The growth of the strain CK1 and ATCC 14580 showed similar trends when cultivated in LB broth either containing 2 ppm ZEN or not. This indicated that ZEN has not affected the growth of CK1 and ATCC 14580.

Example 4

ZEN Detoxification of *Bacillus licheniformis* in LB Broth

Detoxification of *Bacillus licheniformis* under the influence of ZEN was studied after the strain CK1 or ATCC 14580 overnight culture was inoculated into 10 ml of LB broth either containing 2 ppm ZEN or not and incubated at 37° C. with shaking at 250 rpm for 48 h respectively. Samples were taken at 0, 4, 8, 12, 24 and 48 h to extract and quantify ZEN according to Silva et al. (2001).

Figure 4:
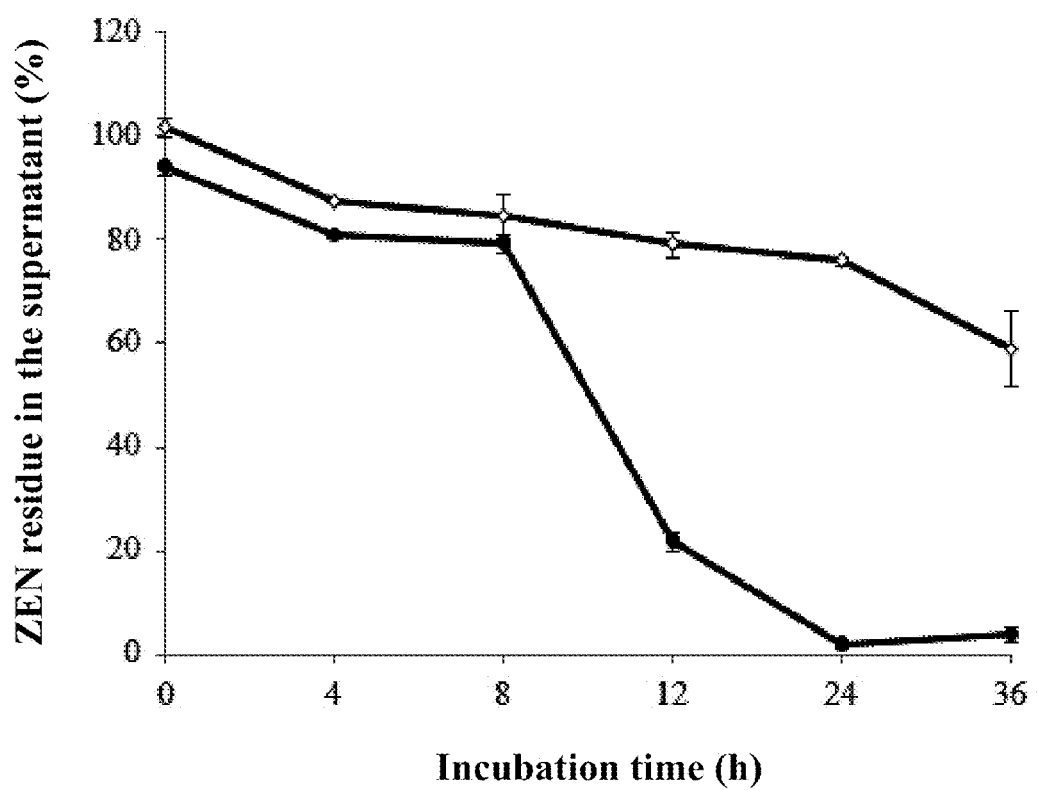
FIG. 4 shows detoxification of zearalenone in the strain CK1 and ATCC 14580.
Figure 5:
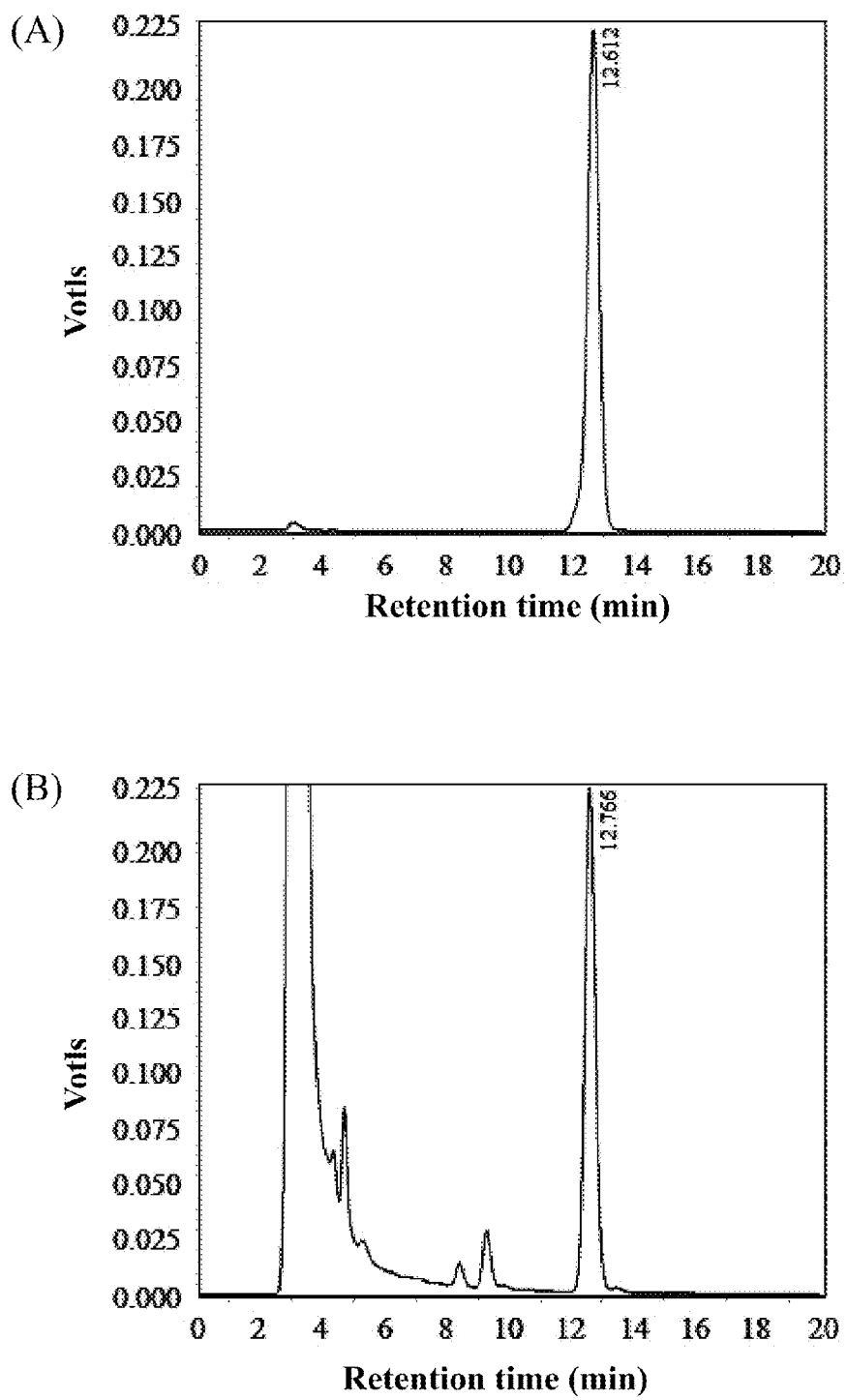
FIG. 5A to 5D display the HPLC analysis results of the strain CK1 and ATCC 14580 cultured LB medium containing zearalenone at different time.
Figure 5:
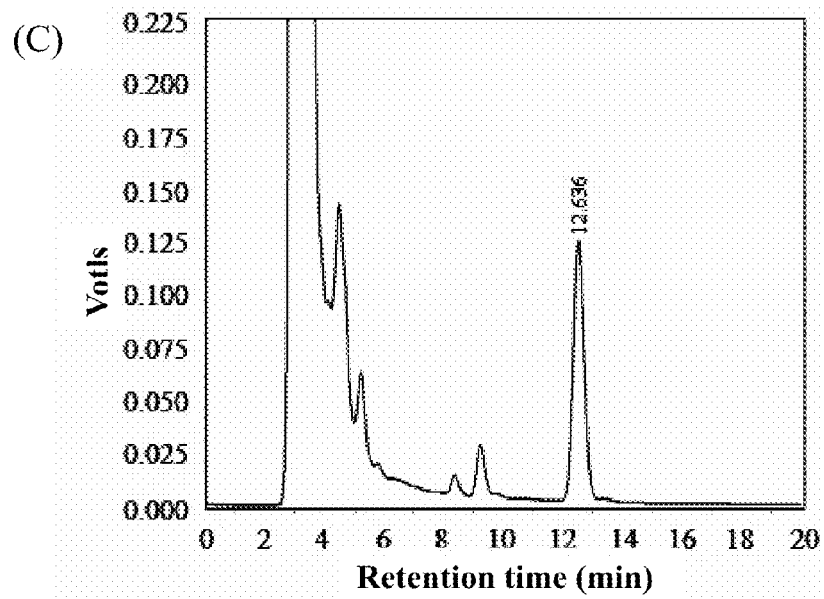
Figure 5:
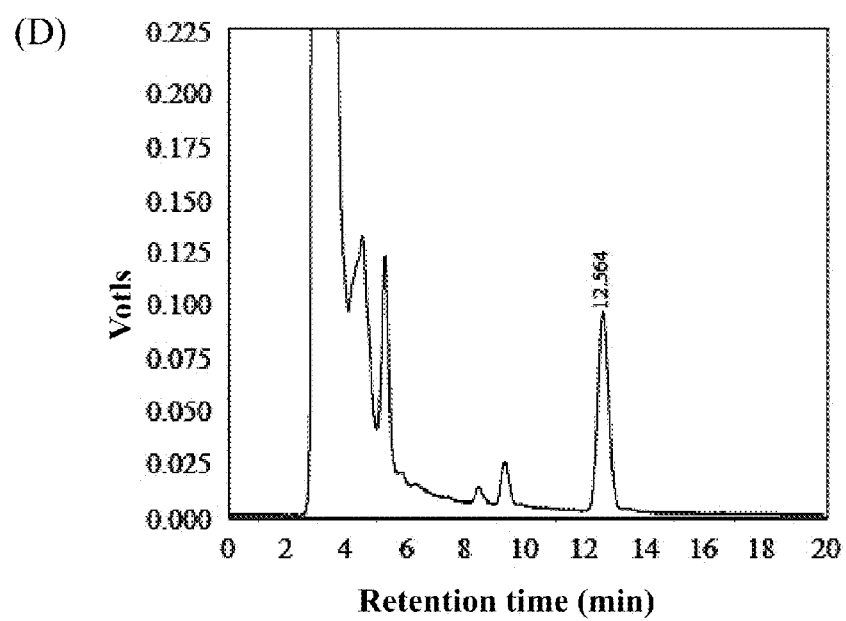

Referring to FIG. 4, both the ATCC 14580 (hollow circle) and the strain CK1 (solid circle) showed detoxification of ZEN. While CK1 displayed a more effective detoxification of ZEN after 8 h of cultivation. Referring to FIG. 5A to 5D, the HPLC analysis results of ZEN containing medium at various time. FIG. 5A displayed the standard of ZEN (retention time: ~12 min), and FIG. 5B to 5D represented the samples of CK1 cultured media after 0 (FIG. 5B), 24 (FIG. 5C), and 48 h (FIG. 5D) cultivation with 2 ppm ZEN. ZEN peak area was decreased with the increase of culture time while other peak areas stayed the same (FIG. 5B-5D). No ZEN peak was observed in CK1 culture medium at 48 h. The peaks shown at 2-6 min retention time should be solvents.

CK1 culture from LB broth containing 2 ppm ZEN for 48 h was centrifuged at 5,000×g for 20 min at 4° C. The cell pellet was resuspended in 10 mM sodium phosphate, pH 7.4 and sonicated with sonicator 3000 (Misoix, Farmingdale, N.Y., USA). The sonicated cell was centrifuged at 12,000×g for 10 min at 4° C. to remove the supernatant. The cell wall in the precipitate was extracted with methanol and analyzed with HPLC to determine the ZEN concentration. No ZEN was found from the extract fractions with HPLC analysis. This indicated that the removal of ZEN in CK1 was not due to cell wall absorption.

Example 5

ZEN Detoxification of *Bacillus licheniformis* in Corn Powder

Corn powder solution was prepared by resuspending 1 g of corn powder containing ZEN in 99 ml of distilled water followed by autoclaving at 121° C. for 15 min. The strain CK1 or ATCC 14580 overnight culture was inoculated into 10 ml of corn powder solution containing ZEN and incubated at 37° C. with shaking at 250 rpm for 36 h respectively. Samples were taken at 0, 12, 24 and 36 h to extract and quantify ZEN according to Silva et al. (2001).

The corn powder was purchased from the local supermarket without ZEN after analysis. The ZEN containing corn powder was prepared according to Maeteo et al. (2001).

Figure 6:
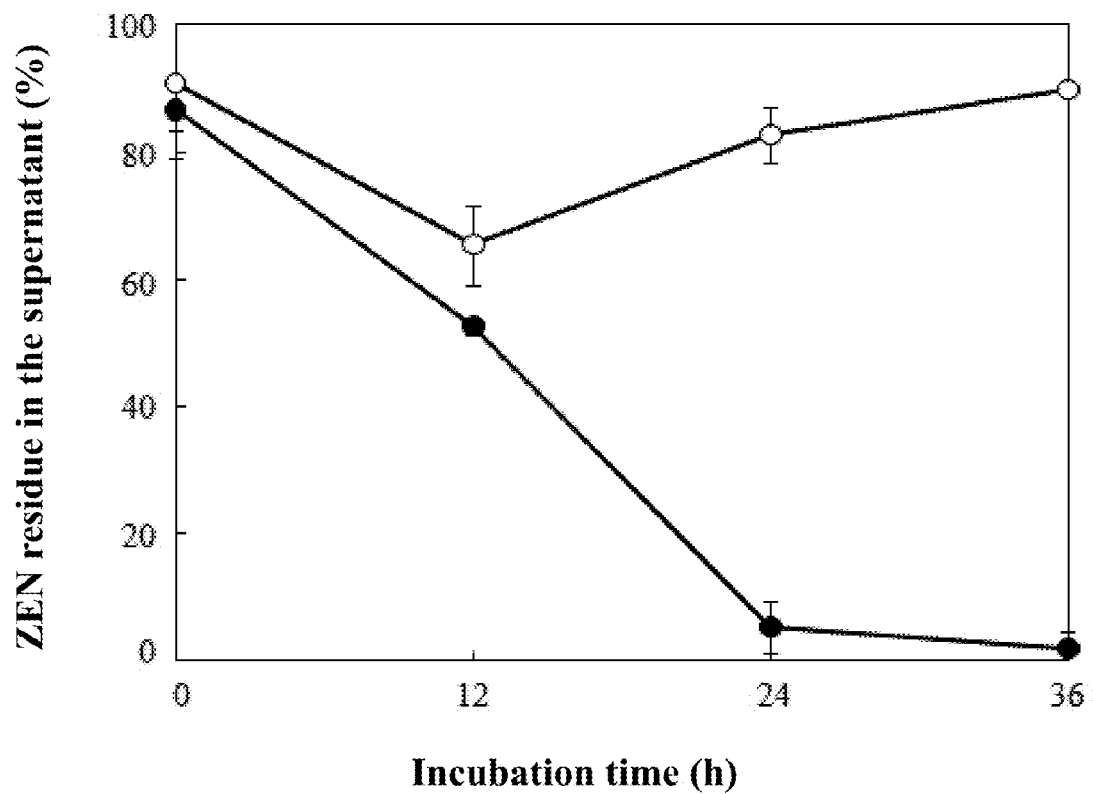
FIG. 6 show the zearalenone detoxification of the strain CK1 and ATCC 14580 in ZEN containing corn powder solution.
Figure 7:
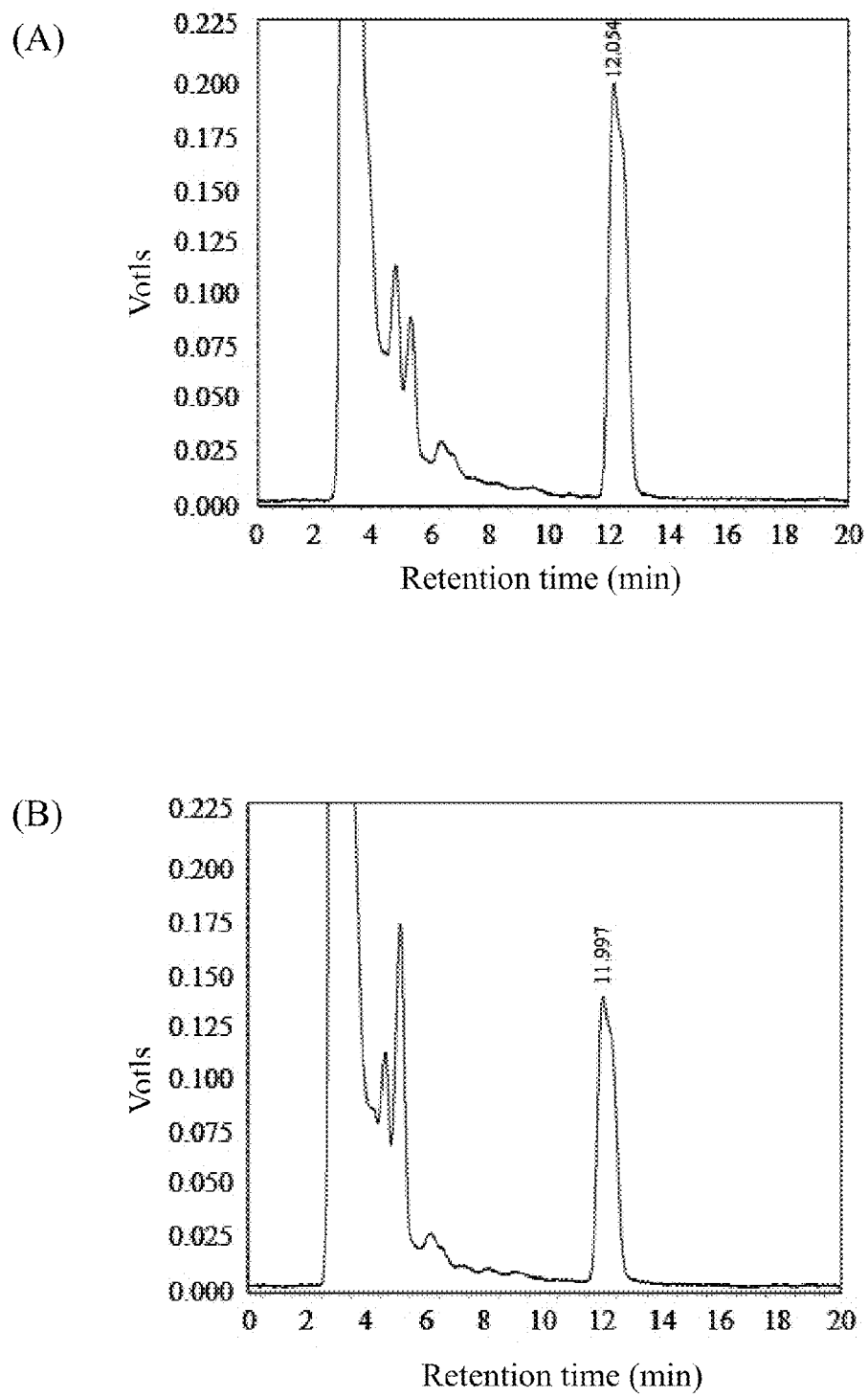
FIG. 7A to FIG. 7D display the HPLC analysis results of the strain CK1 cultured zearalenone containing corn powder solution at different time.
Figure 7:
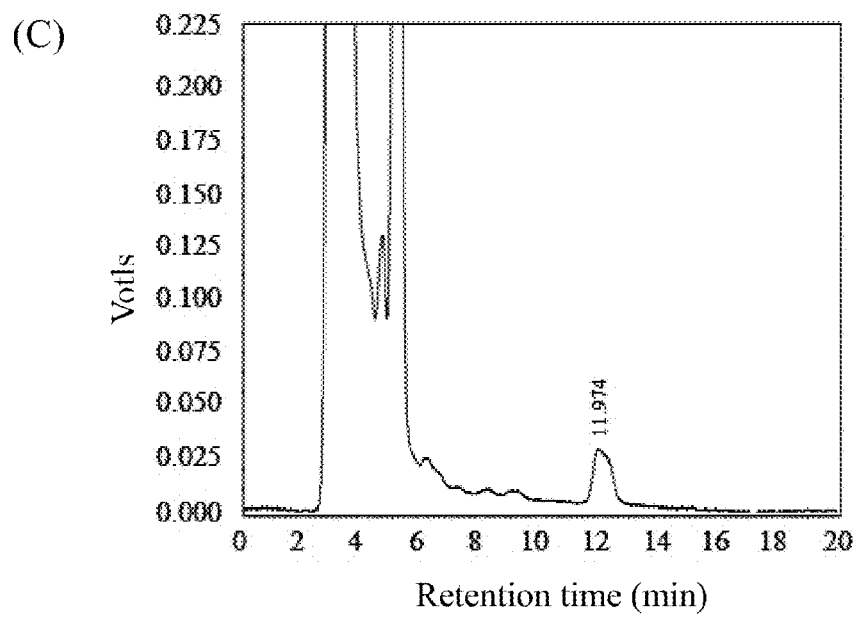
Figure 7:
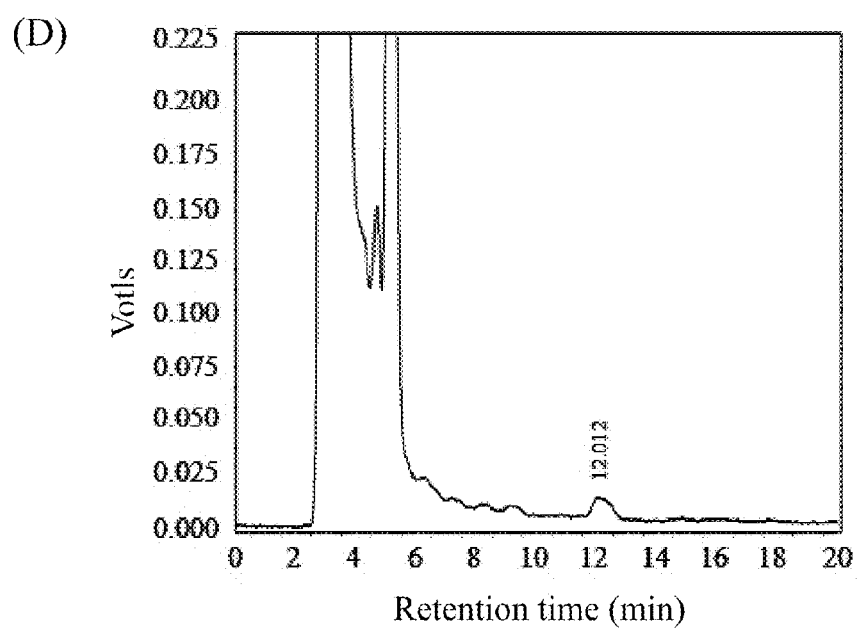

Referring to FIG. 6, the ZEN detoxification of the strain CK1 in ZEN containing corn powder solution was shown. The ZEN concentration in 1% ZEN containing corn powder solution was 1.79±0.15 ppm, which was defined as 100%. FIG. 6 displayed the ZEN detoxification abilities of ATCC 14580 (hollow circle) and CK1 (solid circle) in ZEN containing corn powder solution for 36 h. Only 1.87% ZEN (0.03 ppm) residual was detected in the strain CK1 after 36 h of culture, which confirmed the ZEN detoxification by CK1.

encoded by hblA, hblD, and hblC, respectively. Nhe complex is composed of three proteins NheA, NheB and NheC encoded by genes nheA, nheB, and nheC, respectively.

Immuno-detection kit and PCR were used for detection of enterotoxins and their related genes in the strain CK1. Other strains including *Bacillus licheniformis* ATCC 14580, *B. cereus* ATCC11778, and *B. cereus* ATCC33019 were purchased from ATCC (Manassas, Va.) to serve as control group.

Enterotoxins were detected using BCET-RPLA detection kit (Oxoid, Basingstoke, UK) and TECRA *Bacillus* Diarrheal Enterotoxin Visual Immunoassay (VIA) kit (Tecra Diagnostics, Roseville, Australia) for HblC subunit of Hbl and NheA subunit of the Nhe, respectively Enterotoxin genes including hbl (hblA, hblD, and hblC) and nhe (nheA, nheB, and nheC) of *B. cereus* were detected with PCR according to the methods described by Guinebretiere et al. (2002) and Ouoba et al. (2008). The hblA gene used primer pair BCF (SEQ ID NO: 3) and BCR (SEQ ID NO: 4); the hblB gene used primer pair HAF (SEQ ID NO: 5) and HBR (SEQ ID NO: 6); the hblC gene used primer pair HCF (SEQ ID NO: 7) and HCR (SEQ ID NO: 8); the hblD gene used primer pair HDF (SEQ ID NO: 9) and HDR (SEQ ID NO: 10); the nheA gene used primer pair NH1F (SEQ ID NO: 11) and NH1R (SEQ ID NO: 12); the nheB gene used primer pair NBF (SEQ ID NO: 13) and NBR (SEQ ID NO: 14); the nheC gene used primer pair NCF (SEQ ID NO: 15) and NCR (SEQ ID NO: 16). The results were shown in Table 2, where no toxin related genes were found to be existed in the strain CK1.

TABLE 2

| No. | Bacterial strain | Hbl entertoxin[a] | | | | Nhe entertoxin[a] | | | Tecra kit test index[b] | Oxoid kit test index[c] |
| --- | --- | --- | --- | --- | --- | --- | --- | --- | --- | --- |
| | | hblA | hblB | hblC | hblD | nheA | nheB | nheC | | |
| CK1 | *B. licheniformis* | − | − | − | − | − | − | − | 1 | 0 |
| ATCC 14580 | *B. licheniformis* | − | − | − | − | − | − | − | 1 | 0 |
| ATCC 11778 | *B. cereus* | − | − | − | − | + | + | + | 4 | 128 |
| ATCC 33019 | *B. cereus* | + | + | + | + | + | + | + | 4 | 128 |

[a]+, positive PCR result; −, negative PCR result.
[b]Strains with an index of <3 are considered negative according to the manufacturer's instruction.
[c]Strains with an index of <0 are considered negative according to the manufacturer's instruction.

HPLC analysis results of ZEN on CK1 samples taken at 0, 12, 24 and 36 h was displayed in FIG. 7A to FIG. 7D. The amount of ZEN was significantly decreased in HPLC analysis after CK1 cultivated for 36 h, and no ZEN metabolite was found.

Example 6

Enterotoxin Production in *Bacillus licheniformis* CK1

Pumilus

The microorganisms used in detoxification of mycotoxins should not produce any toxin. Most food poisoning incidents attributed to *Bacillus* species is *B. cereus*, and several other *Bacillus* species were also found to be related. *B. licheniformis* and *B. pumilus* have been associated with food-borne gastroenteritis, which was believed to produce enterotoxin similar to that of *B. cereus*.

The enterotoxins secreted by *B. cereus* include hemolysin BL (Hbl) and nonhemolytic enterotoxin (Nhe). Hbl is a membrane lytic system composed of the proteins B, $L_1$, and $L_2$,

CONCLUSION

*Bacillus licheniformis* was known to produce many degrading enzymes such as protease and amylase. The ATCC 14580 genome contains genes, which encode enzymes to degrade cellulose, semi-cellulose, chitin, pectin or protein. The strain CK1 with xylanase activity in the present invention was isolated from soil samples. It displayed a larger clear zone when compared to ATCC 14580 in the radial diffusion methods with substrates of xylan, carboxymethyl cellulose (CMC) and protein. These results indicated the relatively higher xylanase, CMCase, and protease activities of CK1. Using physiological, biochemical, morphological and 16S rRNA gene sequence analysis methods, CK1 in the invention was identified to be *B. licheniformis*. In addition, ATCC 14580 and CK1 were shown to detoxify ZEN, but CK1 has a relatively better detoxification effects toward ZEN. The strain CK1 in the present invention is the first *Bacillus licheniformis* being disclosed to have such detoxifying effects in the present research field.

Form the abovementioned embodiments, the strain CK1 was shown to decrease the amount of ZEN in culture medium.

No ZEN metabolite was found from HPLC analysis after the strain CK1 cultivated for 48 h. In addition, no ZEN was found from the methanol extract with HPLC analysis. This indicated that the removal of ZEN in the strain CK1 was not due to cell wall absorption.

According to the abovementioned results, *Bacillus licheniformis* CK1 in the present invention can be applied for bio-detoxification of ZEN, such as supplement for food and feed.

The present invention disclosed above is not limited by these examples. The present invention may be altered or modified a bit and all such variations are within the scope and spirit of the present invention.

What is claimed is:

1. An isolated zearalenone (ZEN)-detoxifying *Bacillus licheniformis*, wherein a sample of the *Bacillus licheniformis* has been deposited in the Deutsche Sammlung von Mikroorganismen und Zellkulturen GmbH (DSMZ) with an accession number DSM 025954.

2. A method for detoxifying zearalenone (ZEN) in a food or feed product comprising contacting the food or feed product with the *Bacillus licheniformis* as claimed in claim 1.

3. The method as claimed in claim 2, wherein the *Bacillus licheniformis* contains 20% higher xylanase, CMCase and protease activities than wild type *Bacillus licheniformis*.

4. The method as claimed in claim 2, wherein the method comprises supplementing the *Bacillus licheniformis* into a food.

5. The method as claimed in claim 2, wherein the method comprises supplementing the *Bacillus licheniformis* into a feed.

6. The method as claimed in claim 2, wherein the food or feed product is contacted with the *Bacillus licheniformis* for at least 24 hours.

7. The method as claimed in claim 2, wherein the food or feed product is contacted with the *Bacillus licheniformis* for at least 36 hours.

* * * * *

```
                        SEQUENCE LISTING

<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: primer(16S-27f) for 16S rRNA gene of Bacillus
      Licheniformis

<400> SEQUENCE: 1
agagtttgat cmtggctcag                                               20

<210> SEQ ID NO 2
<211> LENGTH: 20
<212> TYPE: DNA
<213> ORGANISM: Artificial sequence
<220> FEATURE:
<223> OTHER INFORMATION: primer(16S-1492r) for 16S rRNA gene of Bacillus
      Licheniformis

<400> SEQUENCE: 2
cggttacctt gttacgactt                                               20

<210> SEQ ID NO 3
<211> LENGTH: 23
<212> TYPE: DNA
<213> ORGANISM: Artificial sequence
<220> FEATURE:
<223> OTHER INFORMATION: primer(BCF) for hblA gene

<400> SEQUENCE: 3
atgataaaaa aaatccctta caa                                           23

<210> SEQ ID NO 4
<211> LENGTH: 24
<212> TYPE: DNA
<213> ORGANISM: Artificial sequence
<220> FEATURE:
<223> OTHER INFORMATION: primer(BCR) for hblA gene

<400> SEQUENCE: 4
tttgtggagt aacagtttct actt                                          24

<210> SEQ ID NO 5
<211> LENGTH: 20
<212> TYPE: DNA
<213> ORGANISM: Artificial sequence
<220> FEATURE:
<223> OTHER INFORMATION: primer(HAF) for hblB gene

<400> SEQUENCE: 5
aagcaatgga atacaatggg                                               20

<210> SEQ ID NO 6
<211> LENGTH: 20
```

```
<212> TYPE: DNA
<213> ORGANISM: Artificial sequence
<220> FEATURE:
<223> OTHER INFORMATION: primer(HBR) for hblB gene

<400> SEQUENCE: 6
aatatgtccc agtacacccg                                              20

<210> SEQ ID NO 7
<211> LENGTH: 20
<212> TYPE: DNA
<213> ORGANISM: Artificial sequence
<220> FEATURE:
<223> OTHER INFORMATION: primer(HCF) for hblC gene

<400> SEQUENCE: 7
gataccaatg tggcaactgc                                              20

<210> SEQ ID NO 8
<211> LENGTH: 20
<212> TYPE: DNA
<213> ORGANISM: Artificial sequence
<220> FEATURE:
<223> OTHER INFORMATION: primer(HCR) for hblC gene

<400> SEQUENCE: 8
ttgagactgc tcgctagttg                                              20

<210> SEQ ID NO 9
<211> LENGTH: 20
<212> TYPE: DNA
<213> ORGANISM: Artificial sequence
<220> FEATURE:
<223> OTHER INFORMATION: primer(HDF) for hblD gene

<400> SEQUENCE: 9
accggtaaca ctattcatgc                                              20

<210> SEQ ID NO 10
<211> LENGTH: 20
<212> TYPE: DNA
<213> ORGANISM: Artificial sequence
<220> FEATURE:
<223> OTHER INFORMATION: primer(HDR) for hblD gene

<400> SEQUENCE: 10
gagtccatat gcttagatgc                                              20

<210> SEQ ID NO 11
<211> LENGTH: 22
<212> TYPE: DNA
<213> ORGANISM: Artificial sequence
<220> FEATURE:
<223> OTHER INFORMATION: primer(NH1F) for nheA gene

<400> SEQUENCE: 11
gctctatgaa ctagcaggaa ac                                           22

<210> SEQ ID NO 12
<211> LENGTH: 22
<212> TYPE: DNA
<213> ORGANISM: Artificial sequence
<220> FEATURE:
<223> OTHER INFORMATION: primer(NH1R) for nheA gene

<400> SEQUENCE: 12
gctacttact tgatcttcaa cg                                           22
```

```
<210> SEQ ID NO 13
<211> LENGTH: 21
<212> TYPE: DNA
<213> ORGANISM: Artificial sequence
<220> FEATURE:
<223> OTHER INFORMATION: primer(NBF) for nheB gene

<400> SEQUENCE: 13
tttagtagtg gatctgtacg c                                              21

<210> SEQ ID NO 14
<211> LENGTH: 20
<212> TYPE: DNA
<213> ORGANISM: Artificial sequence
<220> FEATURE:
<223> OTHER INFORMATION: primer(NBR) for nheB gene

<400> SEQUENCE: 14
ttaatgttcg ttaatcctgc                                                20

<210> SEQ ID NO 15
<211> LENGTH: 19
<212> TYPE: DNA
<213> ORGANISM: Artificial sequence
<220> FEATURE:
<223> OTHER INFORMATION: primer(NCF) for nheC gene

<400> SEQUENCE: 15
tggattccaa gatgtaacg                                                 19

<210> SEQ ID NO 16
<211> LENGTH: 20
<212> TYPE: DNA
<213> ORGANISM: Artificial sequence
<220> FEATURE:
<223> OTHER INFORMATION: primer(NCR) for nheC gene

<400> SEQUENCE: 16
attacgactt ctgcttgtgc                                                20
```